United States Patent
Michon et al.

(10) Patent No.: US 6,267,961 B1
(45) Date of Patent: *Jul. 31, 2001

(54) DIRECT METHODS FOR MOLAR-MASS DETERMINATION OF FRAGMENTS OF HAEMOPHILUS INFLUENZAE TYPE B CAPSULAR POLYSACCHARIDES AND VACCINE PREPARATION

(75) Inventors: Francis Michon, Laurel; Anello J. D'Ambra, Columbia, both of MD (US)

(73) Assignee: Baxter International Inc., Deerfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/753,242

(22) Filed: Nov. 22, 1996

(51) Int. Cl.$^7$ .................................................. A61K 39/102
(52) U.S. Cl. .................................. 424/193.1; 424/197.11; 424/234.1; 424/256.1; 536/123.1; 530/350; 530/807
(58) Field of Search .............................. 424/256.1, 234.1, 424/193.1, 197.11; 536/123.1; 530/350, 807

(56) References Cited

U.S. PATENT DOCUMENTS

| | | |
|---|---|---|
| 4,356,170 | 10/1982 | Jennings et al. . |
| 4,695,624 | 9/1987 | Marburg et al. . |
| 4,902,506 | 2/1990 | Anderson et al. . |
| 5,034,519 * | 7/1991 | Beuvery et al. ...................... 536/117 |
| 5,679,352 * | 10/1997 | Chong et al. ...................... 424/256.1 |

OTHER PUBLICATIONS

Zion, et al; P and $^{13}$C–N.M.R.–Spectral and Chemical Characterization of the End Group and Repeating–Unit Components of Oligosaccharides Derived by Acid Hydrolysis of *Haemophilus influenzae* Type b Capsular Polysaccharide; *Carbohydrate Research*; pp. 103–121; 1983.

Anderson, et al; Vaccines Consisting of Periodate–Cleaved Oligosaccharides from the Capsule of *Haemophilus influenzae* Type b Coupled to a Protein Carrier: Structural and Temporal Requirements for Priming in the Human Infant; *The Journal of Immunology*; pp 1181–1186; 1986.

Pillai, et al; Distinct Pattern of Antibody Reactivity with Oligommeric or Polymeric Forms of the Capsular Polysaccharide of *Haemophilus influenzae* Type b; *Infection and Immunity*; pp. 4371–4376; 1991.

Egan, et al; Structural Studies and Chemistry of Bacterial Capsular Polysaccharides. Investigations of Phosphodiester––Linked Capsular Polysaccharides Isolated from *Haemophilus influenzae* Types a,b,c, and f: NMR Spectroscopic Identification and Chemical Modification of End Groups and The Nature of Base–Catalyzed Hydrolytic Depolymerization; *Journal of American Chemical Society*; pp 2898–2910; 1982.

Hennessey et al; Molecular Size Analysis of *Haemophilus influenzae* Type B Capsular Polysaccharide; *Journal of Liquid Chromatography*; pp 1715–1729; 1993.

Dubos et al; Human Immunity to the Meningococcus: Preparation and Immunochemical Properties of the Group A, Group B, and Group C Meningococcal Polysaccharides; *The Journal of Experimental Medicine* vol. 129, No. 6 Jun. 1, 1969; pp 1349–1365; 1969.

Gotschlich, et al; Human Immunity to the Meningococcus: Preparation and Immunochemical Properties of the Group A, Group B, and Group C Meningococcal Polysaccharides; *The Journal of Experimental Medicine* vol. 129, No. 6 Jun. 1, 1969; pp 1349–1365; 1969.

Fox et al; Miniaturization of Three Carbohydrate Analyses Using a Microsample Plate Reader; *Analytical Biochemistry—Methods in the Biological Sciences*; pp 93–96; 1991.

Lennarz et al; Guide to Techniques in Glycobiology; *Methods in Enzymology*; vol. 230; pp. 168–199; 1994.

Doner et al; Assay of Reducing End–Groups in Oligosaccharide Homologues with 2,2'–Bicinchoninate; *Analytical Biochemistry Methods in the Biological Sciences*; pp 50–53; 1992.

Porro et al; Modifications of the Park—Johnson Ferricyanide Submicromethod for the Assay of Reducing Groups in Carbohydrates; *Analytical Biochemistry, An International Journal of Analytical and Preparative Methods*; vol. 118, No. 2; pp 301–306; 1981.

Dick et al; Glycoconjugates of Bacterial Carbohydrate Antigens; A Survey and Consideration of Design and Preparation Factors; *Conjugate Vaccines*; pp 48–114; 1981.

Freeman, et al; Correlation of Proton Chemical Shifts by Two–Dimensional Fourier Transform NMR; *Journal of Magnetic Resonance*; vol. 42, No. 1; pp 164–168; Jan. 1981.

Bednar, et al; Molecular Size Analysis of Capsular Polysaccharide Preparations from *Streptococcus pneumoniae*; *Carbohydrate Research*; vol. 243; pp 115–131; 1993.

Beri, et al; Characterization of Chitosans via Coupled Size–Exclusion Chromatography and Multiple–Angle Laser Light–Scattering Technique; *Carbohydrate Research*; vol. 238; pp 11–26; 1993.

Park, et al; *A Submicrodetermination of Glucose*; Journal of Biological Chemistry; vol. 181; pp. 149–151; Nov. 1949.

* cited by examiner

*Primary Examiner*—Jennifer Graser
(74) *Attorney, Agent, or Firm*—Morgan & Finnegan, LLP (57) ABSTRACT

The invention relates to the accurate and precise direct molar-mass measurement of low-molar-mass fragments of polysaccharides such as *Haemophilus influenzae* Type b. The methods for obtaining such determinations for polysaccharides use size-exclusion chromatography (SEC) with detection by multi-angle laser-light-scattering photometry (MALLS) and differential refractometry (RI) and/or (2) determination of polysaccharide fragments and direct measurement of average chain length by quantitative $^1$H NMR, from which molar masses may be derived. Variation between the molar masses obtained by the two methods ranged from 5 to 7%.

6 Claims, 5 Drawing Sheets

DIRECT METHODS FOR MOLAR-MASS DETERMINATION OF FRAGMENTS OF *HAEMOPHILUS INFLUENZAE* TYPE B CAPSULAR POLYSACCHARIDES AND VACCINE PREPARATION

FIELD OF THE INVENTION

This invention relates to the analysis of capsular polysaccharide fragments used for formulating vaccines. More specifically, the invention relates to direct methods for molar mass analysis of fragments of *Haemophilus influenzae* type b capsular polysaccharides. The enhanced precision and accuracy of determining the molar mass of polysaccharide fragments provides for uniform vaccines.

BACKGROUND OF THE INVENTION

The capsular polysaccharide poly(ribosylribitol) phosphate (PRP) of *Haemophilus influenzae* type b (Hib) is the protective immunogen used in commercially available anti-Hib vaccines. This polysaccharide is a linear polymer of the following repeating unit,

[→3)-β-D-Ribf-(1→1)-D-Ribol-(5-PO$_2$→], where n is equal to the number of repeat units (RU) (Ribf, ribofuranose; Ribol, ribitol). To improve the immune response of anti-Hib vaccines in the principal recipients, e.g., infants younger than two years old, the polysaccharide has been synthetically coupled to protein carriers to form neoconjugates. See Dick, W. E., and Beurret, M. (1989) *Contrib. Microbiol. Immunol.* 10, 48–114, and references cited therein. Because of the high average molar mass and wide molar-mass distribution of native PRP (Hennessey, J. P., Jr., Bednar, B.), and (Manam, V. (1993) *J. Liq. Chromatogr.* 16, 1715–1729), conjugates have been prepared from low molar-mass polysaccharide fragments having narrow, reproducible molar-mass distributions. Such fragments have been generated by controlled hydrolysis, (Egan, W., Schneerson, R., Warner, K., and Zon, G. (1982) *J. Am. Chem. Soc.* 104, 2898–2910; Zon, G., and Robbins, J. D. (1983) *Carbohydr. Res.* 114, 103–121), and partial oxidative depolymerization of native polyribosyl ribitol phosphate (PRP). (Anderson, P. W., Pichichero, M. E., Insell, R. A., Betts, R. F., Connuck, D. M., Eby, R., and Smith, D. H. (1986) *J. Immunol.* 137, 1181–1186).

Molar masses of such polysaccharide preparations have been estimated by size-exclusion chromatography (SEC) using as molar mass standards molecules other than PRP. Because such molecules may behave differently than PRP on an SEC column, this calibration method, termed secondary calibration, introduces the potential for significant errors in the determination of the actual site of the polysaccharide to be analyzed (Hennessey, et al.). The use of secondary calibration introduces the potential for significant errors in the determination of the actual size of the polysaccharide to be analyzed. A series of colorimetric and biochemical assays involving analysis of the concentration of reducing end groups (i.e., reducing end group analysis) on the resulting fragments is another method for estimating the size of polysaccharides. This method however suffers from the problem that the standards used may have different functional groups and react differently in the assays than the actual ends of the polysaccharide to be analyzed, thus giving inaccurate results. See Egan et al. supra and Pillai, S., Ciciriello, S., Koster, M., and Eby, R. (1991) *Infect. Immun.* 59, 4371–4376. Because such methods measure molar mass indirectly, they suffer from several limitations arising from their reliance upon initial assumptions about the behavior of the PRP fragments relative to standard compounds. Such assumptions have often proven erroneous. (Hennessey et al. supra and Bednar, B., and Hennessey, J. P., Jr. (1993) *Carbohydr. Res.* 243, 115–130), demonstrated that molar-mass estimation of native PRP and pneumococcal capsular polysaccharides by secondary calibration was not appropriate because of differences in hydrodynamic properties of the secondary standard and the polysaccharide under study. Disadvantages of chemical estimation of molar masses include the tedium of running several assays on the same sample; the necessity of having to rely on assumptions about the uniformity of fragment end groups; and the compounding of error from the mathematical combination of data from the assays.

Another potential error in the reducing-end-group analysis of fragments prepared by partial oxidative depolymerization of PRP (Anderson et al., supra) is the inappropriate use of ribose as a standard. Reducing-end-group analysis is typically done using the Park-Johnson assay (Park, J. T., and Johnson, M. J. (1949) *J. Biol. Chem.* 282, 149–151). Oxidative cleavage of ribitol results in fragments having dissimilar end groups which have different reactivities in the Park-Johnson assay, even though both terminal end groups possess a terminal O-formylmethyl group. (Groups 1 and 2, below). (Seid, R. C., Boykins, R. A., Liu, D. F., Kimbrough, K. W., Hsieh, C. L., and Eby, R. (1989) *Glycoconjugate J.* 6, 489–498).

(1)

-continued (2)

The Park-Johnson assay for detecting reducing end groups in carbohydrates was the only method reported to be used to determine the number average chain length $L_n$, the average number of repeat units per polysaccharide chain) of PRP fragments obtained by oxidative cleavage and used in the vaccines described in Anderson, et al., U.S. Pat. No. 4,902,506. Because ribose was used as the standard for end-group analysis of these fragments, the Park-Johnson assay may have overestimated the average chain length of the fragments by at least 50%, compared to more accurate methods, such as laser-light scattering (LLS), according to data presented below. The data presented below demonstrated that reliance on a single, indirect, colorimetric method for the estimation of molar mass may give erroneous results. Thus, a need exists for precise and consistent methods useful for characterization of vaccines for human recipients.

SUMMARY OF THE INVENTION

The present invention provides a method of determining the absolute molar mass of polysaccharides, including for example PRP used in the preparation of PRP-based vaccines against Hib, by using direct assays of polysaccharides having molar masses in the range of approximately 2,000 and approximately 150,000. In a first assay, size exclusion chromatography (SEC) with on-line detection by multiangle laser-light scattering photometry and differential refractometry (SEC-MALLS/RI) may be used for molar-mass analysis. In a second assay, the end-group structures such as those obtained from oxidative cleavage of PRP (formulas 1 and 2 below), are analyzed by one-dimensional $^1$H nuclear magnetic resonance spectroscopy ($^1$H-NMR). The results of either assay alone or in combination with one another provide a direct and accurate indication of the absolute molar mass of the polysaccharide fragments, unlike the ribose-based indirect measurement systems. The symbol PS in structures 1 and 2 denotes continuation of PRP repeating units, as shown above, including the corresponding opposite end group. End-group structures 1 and 2 thus occur in the same low-molar-mass polysaccharide chain.

By providing accurate determinations of polysaccharide length, this invention also provides superior quality control in the manufacture and analysis of vaccines using polysaccharides, e.g. PRP. Also provided therefore are new vaccines which utilize the more accurately defined polysaccharides.

The accurate molar-mass analysis of polysaccharide fragments also provides, standard reagents which may be used to calibrate other traditional assays used to determine polysaccharide size.

It is an object of this invention to provide a direct method for molar-mass determination of polysaccharide fragments that avoid the use of a ribose standard and therefore accurately determine the molar-mass of the fragments of a vaccine.

It is another object of this invention to combine two direct fragment analysis methods to accurately determine the molar-mass of fragments for a vaccine.

It is still a further object of this invention to prepare a vaccine based upon direct molar-mass analysis techniques to eliminate inaccuracies of ribose-based techniques.

Another object of this invention is to provide a vaccine containing polysaccharide fragments having the following repeat unit:

wherein there are between 10 and 30 repeat units per fragment.

A further object of this invention is a vaccine from polysaccharide fragments having molar masses in the range of approximately 5,000 to approximately 10,000 inclusive.

Another object of this invention is to combine two molar-mass determination techniques of polysaccharide fragment analysis, i.e., measurement of separated fragments by SEC-MALLS/RI and analysis of separated fragments by one-dimensional $^1$H-NMR to eliminate inaccuracy of ribose-based determination techniques.

These and other objects and advantages of the invention will become more apparent from the following detailed description, examples and annexed drawings.

DETAILED DESCRIPTION OF THE INVENTION

This invention relates to the preparation of vaccines based upon direct molar-mass analysis techniques to eliminate inaccuracies of ribose-based methods. More specifically, the invention relates to direct methods for molar-mass analysis of polysaccharide fragments. The enhanced precision and accuracy of determining the molar mass of polysaccharide fragments according to this invention provides for more uniform vaccines. The term "direct" as used to describe this invention shall refer to methods of analysis which detect the polysaccharide fragments under analysis rather than by comparison to other molecules which would be used as a reference.

According to this invention, absolute molar-mass information is used in the preparation of polysaccharide-based vaccines by using direct assays for molar-mass determination of polysaccharides. For vaccines utilizing Hib polysaccharides, molar masses in the range of approximately 5,000 to approximately 10,000, inclusive are preferred.

The more accurately defined polysaccharides provided by this invention may be used with any of the techniques known in the art for preparing haemophilus influenzae type b vaccines. Such vaccines are described in, for example, contributions to Microbiology and Immunology, Vol. 10: Conjugate Vaccines, Editors J. M. Cruse and R. E. Lewis, Jr. (1989), U.S. Pat. Nos. 4,356,170, 4,902,506 and 4,695,624, which are incorporated herein by reference.

In a first assay, size exclusion chromatography (SEC) with on-line detection by SEC-MALLS/RI is used for direct mass analysis of polysaccharide fragments such as those derived from PRP. In a second assay, end-group structures 1 and 2 of [O]-PRP fragments are evaluated by $^{1}$H-NMR, and the resulting data used to determine the absolute mass of the fragments.

Zon and colleagues (Egan, et al., supra; Zon and Robbins, supra) previously reported end-group analysis NMR for PRP oligosaccharide fractions obtained by base- and acid-catalyzed hydrolytic depolymerization. Hydrolysis of PRP resulted in complex mixtures of end groups whose complete analysis entails $^{31}$P-NMR methods for base-catalyzed hydrolyzates or a combination of $^{31}$P- and $^{13}$C-NMR experiments for acid-catalyzed hydrolyzates. In contrast, [O]-PRP fragments in the present invention are amenable to analysis by $^{1}$H-NMR, which is ordinarily more practical than $^{31}$P- and $^{13}$C-NMR. (Egan et al. (1982) J. Am. Chem. Soc. 104, 2898–2910) and Robins above.

An advantage of determining molar-mass of polysaccharides according to this invention is that more accurate determinations of molar-mass are obtained. Accordingly, it is therefore possible to determine with greater accuracy optimum sizes of polysaccharides which should be used in the production of polysaccharide vaccines, including vaccines using polysaccharides alone, or those in which the polysaccharide is conjugated to protein.

Based on the more accurate determinations of PRP provided by this invention, preferred molar-masses of PRP polysaccharides to be used in the production of PRP protein conjugate vaccines are between about 2000 and 15,000, and more preferably between about 5,000 and 10,000. Using the method of molar-mass determination provided by this invention to determine the number of repeat units, PRP fragments of between about 5.5 and 40 and more preferably 13.5 to 27 repeat units are used to prepare the Hib vaccines of this invention.

EXAMPLES

Reagents

Unless otherwise noted, reagents were analytical grade or better and were used as supplied. Cupric sulfate pentahydrate and ferric chloride hexahydrate were obtained from Aldrich Chemical Co. (Milwaukee, Wis.). Ethylene glycol, concentrated hydrochloric acid, orcinol monohydrate, and sodium metaperiodate ($NaIO_4$) were supplied by J. T. Baker, Inc. (Phillipsburg, N.J.). Sodium azide was supplied by Fisher Scientific Co. (Pittsburgh, Pa.). Glycolaldehyde dimer (99.0%) and ribose (99.5%) were obtained from Fluka Chemical Co. (Ronkonkoma, N.Y.). Blue Dextran 2000 was obtained from Pharmacia Biotech, Inc. (Piscataway, N.J.). Coomassie Plus protein assay reagent was supplied by Pierce Chemical Co. (Rockford, Ill.). Dextran fractions D 9260 (nominal molar mass, as provided by the supplier, 9200), D 4626 (nominal molar mass 19,200), and D 4133 (nominal molar mass 39,100), 4,4'-dicarboxy-2,2'-biquinoline disodium salt (BCA) disodium salt, human IgG, and L-serine were supplied by Sigma Chemical Co. (St. Louis, Mo.). Ultra-high-purity water ($\sigma \geq 18$ Mohm $cm^{-1}$) was supplied by Baxter/Scientific Products (McGaw Park, Ill.), and deuterium oxide ($D_2O$), 99.9 atom-% D) was obtained from Isotech, Inc. (Miamisburg, Ohio).

Isolation and Purification of PRP

Haemophilus influenzae strain Eagan was obtained from the Rockefeller University (New York, N.Y.). Crude PRP was isolated as the calcium salt from culture supernatants by a modification of the procedure of Gotschlich, et al. for the isolation of meningococcal capsular polysaccharides (Gotschlich, E. C., Liu, T. Y., and Artenstein, M. S. (1969) J. Exp. Med. 129, 1349–1365, incorporated herein by reference). The polyanionic species (PRP and nucleic acids) were precipitated with hexadecyltrimethylammonium bromide, the precipitate was extracted with aqueous $CaCl_2$ and nucleic acids were removed from the extract by fractional precipitation with ethanol. The polysaccharide was further purified by diafiltration against 2 mM sodium phosphate, pH 7.2, and water through a MiniKros 50,000 molecular-weight cutoff, polysulfone hollow-fiber (Microgon, Inc., Laguna Hills, Calif.).

Oxidative Partial Depolymerization of PRP

Reaction conditions were determined by running several parallel small-scale reactions with varying concentrations of $NaIO_4$. The amount of $NaIO_4$ for the large-scale reaction was that concentration giving a distribution of [O]-PRP fragments with average molar mass of approximately 10,000, (approximately $L_n$29), as determined by SEC-MALLS/RI. In the large-scale reaction, sodium PRP (612 mg, 1.66 mmol of repeat units) was dissolved in Dulbecco's phosphate-buffered saline (PBS) to achieve a concentration of 20 mg/ml and was treated with 30.6 ml of 7 mM $NaIO_4$ (0.13 mol/mol PRP repeating units) in PBS. The reaction mixture was stirred in the dark for 2 hr. at room temperature. Excess 1 M aqueous ethylene glycol was added to quench the oxidation reaction and stirring was continued for 30 minutes in the dark. The reaction mixture was diafiltered sequentially against 1 M NaCl and water with an Amicon TCF-10 concentrator equipped with a Diaflo YM-3 membrane (Amicon, Inc., Beverly, Mass.); the final retentate was lyophilized.

The [O]-PRP preparation was purified and fractionated by SEC on Superdex 200 PG, and the effluent containing

[O]-PRP was collected in seven fractions. Five fractions were eluted from the Superdex column in the relative-elution-volume ranges $0.33<K_{av}\leq0.41$ (fraction I) and $0.41<K_{av}\leq0.50$ (fraction II), $0.50<K_{av}\leq0.58$ (fraction III), $0.58<K_{av}\leq0.67$ (fraction IV), and $0.67<K_{av}\leq0.75$ (fraction V). Fractions were dialyzed at 4° C. against water in cellulose tubing (SpectraPor, Spectrum Medical Industries, Inc., Houston, Tex.) having a molecular-weight cutoff of 1000 (for fraction V) or 3500 (for fractions I–IV); the retentates were lyophilized. Each of these fractions were analyzed by SEC on Superose 12, as described below, to obtain their individual $K_{av}$s.

Example 1

A. Analysis of PRP Using SEC Methods

Analytical SEC was done on a Pharmacia FPLC system equipped with a Pharmacia model UV-1 ultraviolet detector (with 280-nm filter), a Waters Corp. (Milford, Mass.) model R401 differential refractometer, and a Pharmacia Superose 12 HR 10/30 column. The column was eluted at 0.75 ml/min with PBS, pH 7.4. Preparative SEC was done on a Pharmacia system comprising the above-mentioned detectors, a model P-1 peristaltic pump, a FRAC-100 fraction collector, and an XK 26/100 column packed with Superdex 200 PG (Pharmacia). The column was eluted with PBS at 1.7 ml/min. and fractions of ~5 ml were collected. Blue Dextran 2000 was used to determine the void volume ($V_o$) and sodium azide the total bed volume ($V_t$) for both columns. Relative elution volumes were expressed as $K_{av}=(V_e-V_o)/(V_t-V_o)$, in which $V_e$ is elution volume from the RI profile.

Glycans (PRP, [O]-PRP fractions, or dextran standards) were analyzed by laser-light-scattering photometry and fractionated on a Hewlett-Packard (Mountain View, Calif.) 1090 Series II liquid chromatography system equipped with a Superose 12 HR 10/30 column and eluted with PBS at 0.75 ml/min. The mobile phase was prepared in ultra-high-purity water and filtered through a 25-mm diameter in-line filter (Millipore Corp., Marlborough, Mass.) equipped with a Millipore type GV 0.22μm membrane. Glycan samples (~2 mg each) were dissolved to 10 mg/ml in a mobile phase, and the resulting solutions were centrifuged for 2 to 3 min at 14,000 rpm to remove particulates before injection. Column effluents were directly analyzed with a miniDAWN fixed-triple-angle laser-light-scattering photometer (Wyatt Technology Corp., Santa Barbara, Calif.) coupled to a Hewlett-Parkard model 1047A differential refractometer. Solvent delivery and sample injection in the LC unit were controlled with the Hewlett-Packard ChemStation HPLC software package. The mini-DAWN's light source was a 20-mW linearly polarized semiconductor diode laser providing radiation of 690 nm. The analog signal output of the refractometer was connected to the miniDAWN through an auxiliary input channel. Light-scattering data were acquired and processed with Wyatt's ASTRette program. Peak area was calculated by the Wyatt software as the summation of the area of 200–300 trapezoidal divisions or "slices" over the full range of a peak. The weight-average molar mass ($M_w$) and number-average molar masses ($M_n$) of a polysaccharide eluding in a given peak were then calculated by the software from the area so obtained. The differential refractive index increment (dn/dc), a parameter required for the calculation of $M_w$ and $M_n$, was determined to be 0.140 g/mL using the HP 1047A refractometer on-line. This value is comparable with values previously obtained for other polysaccharides.

B. Analysis of PRP Using NMR Methods

One-dimensional $^1$H-NMR spectra was recorded at 500 MHz on a Bruker Instruments (Billerica, Mass.) model AMX 500 spectrometer equipped with a 5-mm inverse broad-band probe. Samples (2–3 mg) are each dissolved in 0.5 ml of $D_2O$ in 5-mm tubes. Chemical shifts are referenced to internal acetone (δ2.225). For the calculation of $M_n$, spectra of all samples were recorded under identical conditions, including the following parameters: sweep width, 6024 Hz; digital resolution, 0.37 Hz/point; pulse width, 3.0 μs (45° pulse angle); acquisition time, 1.4 sec; recycle delay, 2.0 sec. Resonances integrated for the calculation of $M_n$ were the anomeric proton of the ribofuranosyl residue (δ5.063, d) and the highest-field methylene proton (δ3.523, dd) of one of two hydrated, terminal O-formylmethyl groups. Assignment of this resonance was verified by a two-dimensional homonuclear $^1$H COSY experiment (Bax, A., Freeman, R., and Morris, G. (1981) *J. Magn. Reson* 42, 164–168, incorporated herein by reference) performed on selected [O]-PRP fractions (data not included).

The indirect techniques of the prior art that were compared with the methods of the present invention include a microscale colorimetric method combining an assay in which the response of ribose is compared to that of a compound whose structure is closely related to that of the O-formylmethyl group.

C. Results-Comparison I

1. Chemical Analyses

Protein was determined by the Bradford method (Bradford, M. M. (1976) *Anal. Biochem.* 195, 93–96, incorporated herein by reference) with Coomassie Plus reagent and human IgG as standards. Nucleic acid content was estimated by direct ultraviolet photometry at 260 nm. Photometric measurements were made with a Shimadzu model UV160U spectrophotometer.

Total pentose in the [O]-PRP preparations was determined by a modification of the microscale orcinol/$Fe^{3+}$/HCl assay of Reuter and Schauer (Reuter, G., and Schauer, R. (1994) *Methods Enzymol.* 230, 168–199, incorporated herein by reference). Briefly, 200 μl of reagent was added to 200 μl of solution containing up to 15 μg of ribose (dispensed as aliquots of a 500 μm solution) as standard or up to 70 μg of polysaccharide-containing material (from 1.2–1.5 mg/ml test solutions). Samples, in 1.5-ml microcentrifuge tubes, were mixed well and heated in boiling water for 15 minutes. After cooling for 5 minutes on ice, the samples were transferred to a flat-bottom, 96-well, low-binding polystyrene microtiter plate (Corning, Inc.; Corning, N.Y.) and read at 650 nm in a Molecular Devices (Menlo Park, Calif.) Emax microplate reader.

Terminal O-formylmethyl group (reducing-end group) content was determined colorimetrically by the microscale BCA method (Fox, J. D., and Robyt, J. F. (1991) *Anal. Biochem.* 195, 93–96, incorporated herein by reference) on samples containing up to 25 nmol of ribose or glycolaldehyde monomer as standard (from 50 and 500 μM solutions) or up to 70 μg of polysaccharide (corrected for pentose content, from the test solutions described above). The assay was run in a microtiter plate, in which samples were read at 560 nm with reference set at 650 nm.

2. PRP and [O]-PRP Fractions

The purified PRP prepared for this study is 89.8% pure, by ribose content, and contained 0.3% protein and 0.06% nucleic acid. The average molar mass of the polysaccharide could not be precisely determined by SEC-MALLS/RI in the present instrumental configuration, although $M_w$ was estimated to be in excess of 105,000, the value reported for native PRP by Hennessey, et al., supra. Controlled partial oxidative depolymerization of the polysaccharide gave a mixture of fragments which was sized by preparative SEC on Superdex 200 PG into seven fractions, the middle five of which were further characterized. Their purities and relative elution volumes (as $K_{av}$) by analytical SEC on Superose 12 are given in Table 1.

TABLE 1

Properties of [O]-PRP Fractions

| Fraction | $K_{av}$[a] | Purity (%)[b] |
|---|---|---|
| I | 0.22 | 68.7 |
| II | 0.26 | 71.5 |
| III | 0.32 | 77.6 |
| IV | 0.36 | 75.7 |
| V | 0.43 | 94.2 |

[a]Determined by analytical SEC-RI on Superose 12 HR.
[b]Calculated in two steps from orcinol/$Fe^{3+}$/HCl assay data:

(1) µg pure polysaccharide=(µg total Rib)(368 g/mol NaPRP repeat units)/150 g/mol Rib
(2) % purity=(µg pure polysaccharide/µg solid sample)×100

3. Absolute Molar Mass by SEC-MALLS/RI

The applicability of SEC-MALLS/RI to the analysis of short fragments derived from PRP was similar to the characterization of PRP and other polysaccharides. To this end, [O]-PRP fractions I–V were analyzed by SEC-MALLS/RI to obtain their absolute molar masses. A series of dextran fractions was also analyzed in order to construct a secondary calibration curve for comparison (Table 2).

TABLE 2

Molar Mass Data for Dextrans

| Sample | $K_{av}$ | $M_w$ (kg/mol) | $M_n$ (kg/mol) | Polydispersity $M_w/M_n$ |
|---|---|---|---|---|
| D-4133 | 0.25 | 40.5 ± 0.40 | 31.5 ± 0.59 | 1.29 |
| D-4626 | 0.39 | 15.8 ± 0.20 | 12.2 ± 0.40 | 1.30 |
| D-9260 | 0.44 | 9.78 ± 0.54 | 8.30 ± 0.46 | 1.18 |

[a]Determined by separate analytical SEC-RI on Superose 12 HR
[b]Mean ± standard deviation (SD) from triplicate analyses by SEC-MALLS/RI The dextrans and PRP oligosaccharide fraction III were analyzed in triplicate to establish the reproducibility of the method; the remaining oligosaccharide fractions were analyzed only once because of the limited amounts of these materials. The relative standard deviations (RSD; RSD=SD÷mean, expressed as percent) of the mean molar masses determined from all triplicate analyses did not exceed 1.5%; variabilities of less than 5% have been obtained in other SEC-MALLS/RI studies of polysaccharides. Sample recovery, the ratio of sample mass eluted (as calculated by ASTRA) to sample mass injected, is greater than 90% for dextrans and 85% or greater for PRP oligosaccharides. These levels are considered acceptable for SEC experiments.

Shown in Table 3 are the molar mass data derived from the SEC-MALLS/RI analyses of the [O]-PRP fractions.

TABLE 3

Molar Masses of [O]-PRP Fractions by SEC-MALLS/RI and by Secondary Calibration

| | SEC/MALLS/RI data | | | Secondary Calibration |
|---|---|---|---|---|
| Sample | $M_w$ (kg/mol) | $M_n$ (kg/mol) | Polydispersity ($M_w/M_n$) | $M_w$ (kg/mol) |
| I | 17.4 | 17.1 | 1.01 | 51 |
| II | 13.1 | 12.9 | 1.02 | 36 |
| III | 10.2 ± 0.26[a] | 9.86 ± 0.10[a] | 1.03 | 27 |
| IV | 7.24 | 7.03 | 1.03 | 17 |
| V | 5.08 | 4.76 | 1.07 | 11 |

[a]Mean ± SD from triplicate analyses

The ratio of weight-average ($M_w$) to number-average ($M_n$) molar masses, or polydispersity, is an indication of the breadth of a molar-mass distribution. The low polydispersity values (<1.1) of the [O]-PRP fractions thus indicates that their molar-mass distributions are narrow. Data from the analysis of the dextran fractions by SEC-MALLS/RI was used to generate the secondary calibration curve (Table 2) which has polydispersities (>1.2) that reflect their broad molar-mass distributions.

Figure 1:
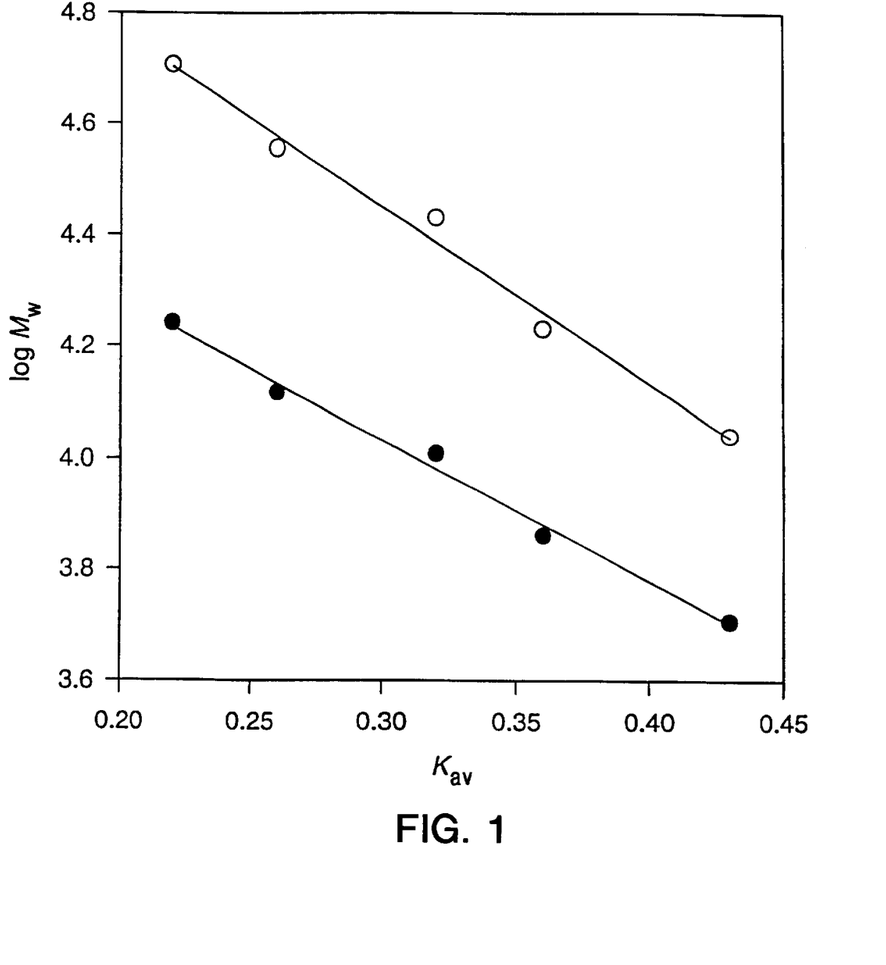
FIG. 1: Comparison of molar-mass determinations of [O]-PRP fractions by SEC-MALLS/RI (·) and by SEC using dextrans as secondary molar-mass calibrants (○).
Figure 2:
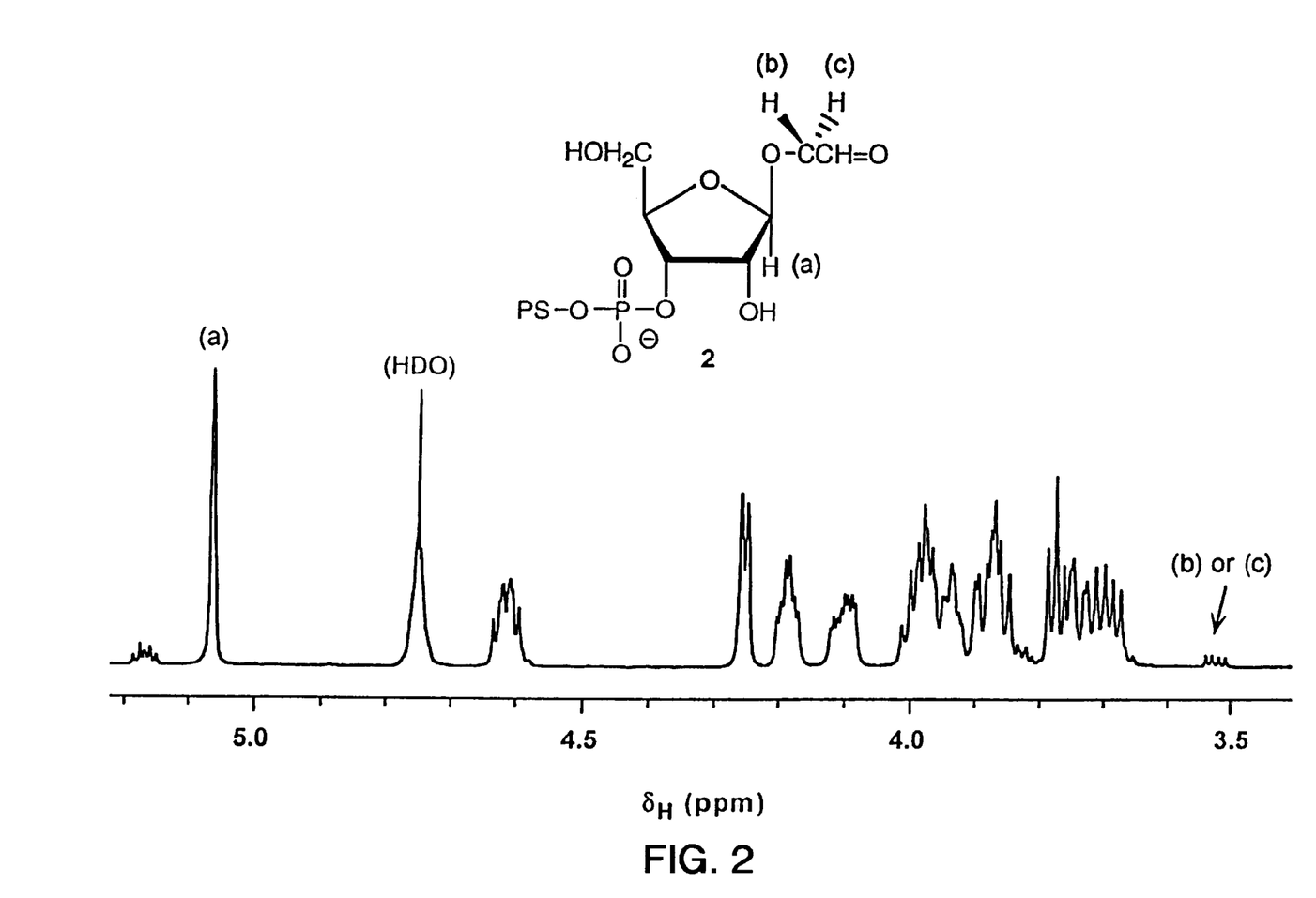
FIG. 2: 500 MHz $^1$H-NMR spectrum of [O]-PRP fraction V. Resonances used in NMR end-group analysis are labelled.

The molar-mass data (as $M_w$) obtained using multi-angle laser-light scattering (MALLS) detection and the relative elution volumes (as $K_{av}$) for the PRP fragments were plotted (FIG. 1) as a comparative basis for all other methods for molar-mass determination. The resulting semilog plot is linear ($r^2=0.992$) through the entire molar-mass range. Molar-mass data from the secondary calibration with dextran (Table 3) were plotted alongside the primary curve in FIG. 2. The secondary calibration overestimates the molar masses of the [O]-PRP fractions by as much as 2.5-fold. Although the [O]-PRP fragments and the dextran fractions eluted in the same range of relative volumes, the use of dextrans as secondary molar-mass calibrants was shown to be inappropriate in this case. These results confirm previous findings of the inapplicability of secondary calibration in SEC analysis of polysaccharides. (Hennessey et al., supra; Bednar and Hennessey, supra; Beri, R. G., Walker, J., Reese, E. T., and Rollings, J. E. (1993) Carbohydr. Res. 238', 11–26).

4. Absolute Molar Mass by NMR End-Group Analysis

The terminal O-formylmethyl groups of the PRP fragments were formed by oxidative cleavage of the intact polysaccharide and provide excellent reporter groups for the direct measurement of $L_n$ in a single one-dimensional $^1$H-NMR experiment. The resonances used (FIG. 2) were chosen because they are well separated from other resonances, i.e., they are each flanked by enough flat baseline to permit proper integration. The $L_n$ was calculated from the equation $A_1/A_2$, in which $A_1$ is the relative peak area of the resonance of the anomeric proton of the Ribf residue (δ5.063) and $A_2$ is the relative peak area of the upfield resonance of one of the methylene protons of one of the terminal O-formylmethyl groups (δ3.523). The chemical shift and multiplicity (double doublet) of the methylene resonance suggest that this O-formylmethyl group is the aglycon of the terminal ribofuranosyl residue (i.e., structure 1).

Figure 3:
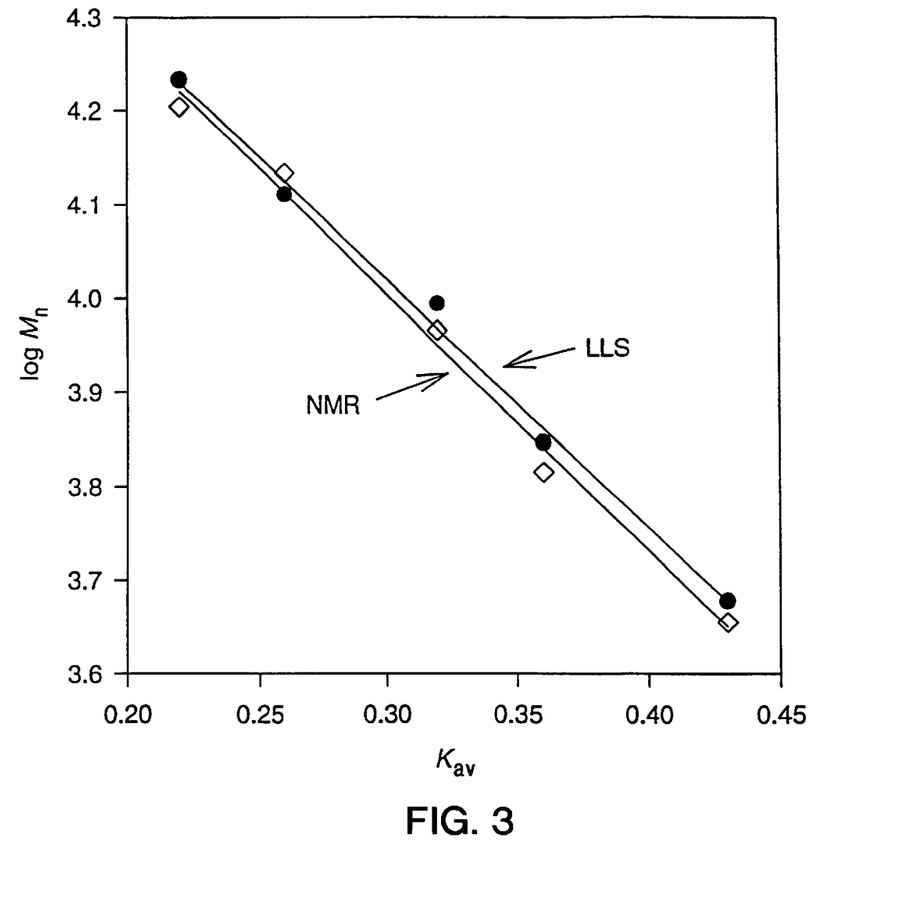
FIG. 3: Comparison of molar-mass determinations of [O]-PRP fractions by SEC-MALLS/RI(·) and by quantitative $^1$H-NMR(◊). Regression lines are labelled for clarity.

Molar-mass data derived from NMR integrals (Table 4) were plotted, as log $M_n$, against the relative elution volumes of the polysaccharide fractions alongside the analogous LLS data (FIG. 3). The molar masses from NMR analysis were in excellent agreement with the LLS values, their linear regression curves being nearly collinear. Variation of the NMR values from the LLS values ranged from 5 to 7%. No significant deviation from linearity was observed for the higher molar-mass fragments due to the expected progressive decrease in the signal-to-noise ratio (S/N) of the methylene resonance with increase in chain length.

TABLE 4

Molar Masses of [O]-PRP Fractions by $^1$H-NMR Analysis

| Sample | NMR data $L_n^{a,b}$ | $M_n$(kg/mol)$^c$ | SEC/MALLS/RI data $L_n^{b,d}$ |
|---|---|---|---|
| I | 46 | 16.0 | 49 |
| II | 39 | 13.6 | 37 |
| III | 27 | 9.24 | 28 |
| IV | 19 | 6.54 | 20 |
| V | 13 | 4.52 | 14 |

$^a$Calculated as described in the text.
$^b$Rounded to the nearest integer.
$^c M_n = 100 + [(L_n) (345 \text{ g/mol PRP repeat units})]$; 100 g/mol = approx. total mass of the two end groups.
$^d L_n = (M_n - 100)/345$; $M_n$ in g/mol, taken from Table 3.

5. Estimation of Molar Mass by Colorimetry

In the colorimetric estimation of $M_n$ of the fractions, two steps are required: (1) determination of total ribose content, from which oligosaccharide purity was calculated, and (2) quantitation of the terminal O-formylmethyl groups by a reducing end-group assay. The total ribose content was determined by an adaptation of a microscale orcinol/Fe$^{3+}$/HCl assay (Reuter and Schauer, supra), originally intended for the analysis of sialic acids, in which samples were read in a 96-well microtiter plate on a microplate reader. The assay gives excellent linearity ($r^2=0.9997$) in the range of 3–15 μg of ribose with very good reproducibility, with RSDs averaging 3.3% for triplicate analyses. This modification of the orcinol assay for total ribose represents a significant increase in convenience and efficiency over earlier methods, e.g., as described by Dische, Z. (1962) Methods Carbohydr. Chem. 1, 484–488, as cited by Seid, et al, supra. Purities of the [O]-PRP fractions were calculated and are described in Table 1 above.

The content of reducing-end groups was quantitated by the Cu$^{2+}$/BCA assay (Fox and Robyt, supra) which has a redox chemistry comparable to that of the Park-Johnson ferricyanide assay. Conditions under which this assay was used to detect reducing-end groups in [O]-PRP fragments must ensure that end groups react uniformly regardless of molecular size. Such conditions were established for the analysis of homologous series of oligosaccharides of glucose, N-acetylglucosamine, and galacturonic acid. (Doner, L. W., and Irwin, P. L. (1992), Anal. Biochem, 202, 50–53). A miniaturized version of the BCA assay was used under conditions established for reducing-end-group analysis.

Standard curves for the BCA assay were constructed using glycolaldehyde and ribose. Previously, ribose was used as the standard in the Park-Johnson reducing-end-group analysis of PRP fragments derived by oxidative cleavage. Studies of both assays demonstrate significant variations in the color yields of various monosaccharides. (Doner and Irwin, supra; Porro, M., Viti, S., Antoni, G., and Neri, P. (1981), Anal. Biochem, 118, 301–306). Because glycolaldehyde was the structural precursor of the terminal O-formylmethyl groups of the [O]-PRP fragments, the reactivity of this compound in the BCA assay should closely approach that of O-formylmethyl groups. Comparing the responses of ribose and glycolaldehyde shows that glycolaldehyde is a more suitable standard for colorimetric reducing-end-group analysis of [O]-PRP fragments.

Figure 4:
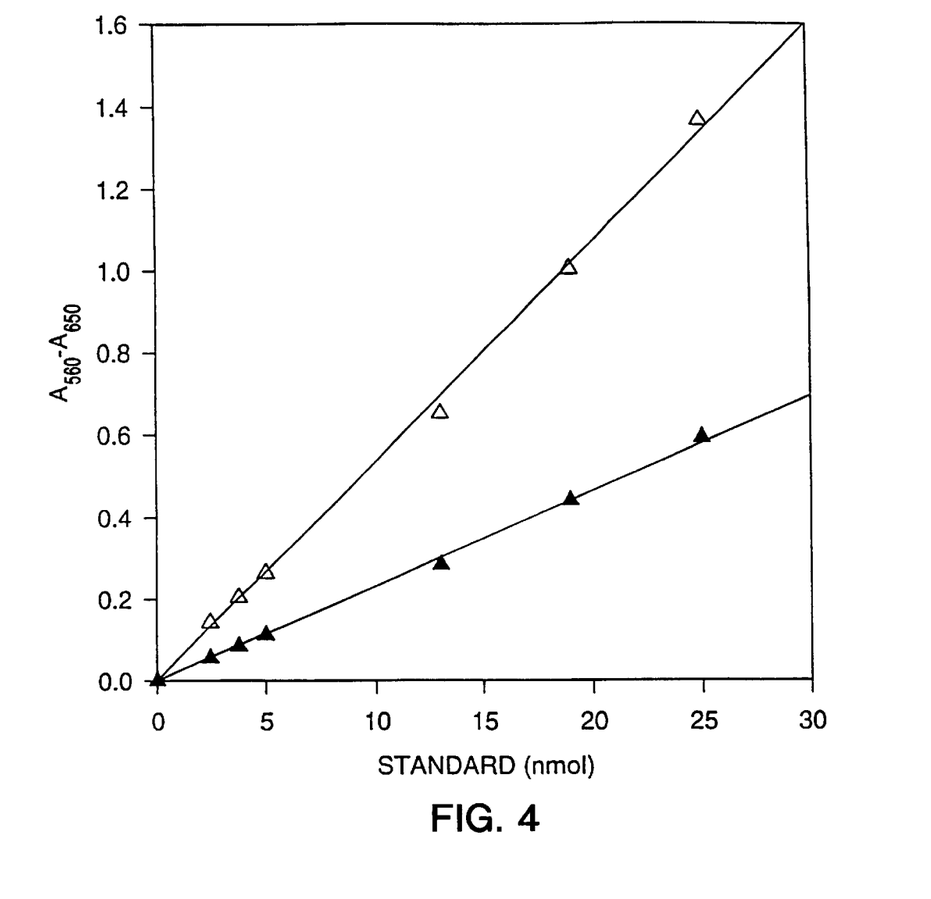
FIG. 4: Standard curves, using glycolaldehyde (▲) and ribose (Δ), for estimation of reducing-end groups by the $Cu^{2+}$/BCA procedure.
Figure 5:
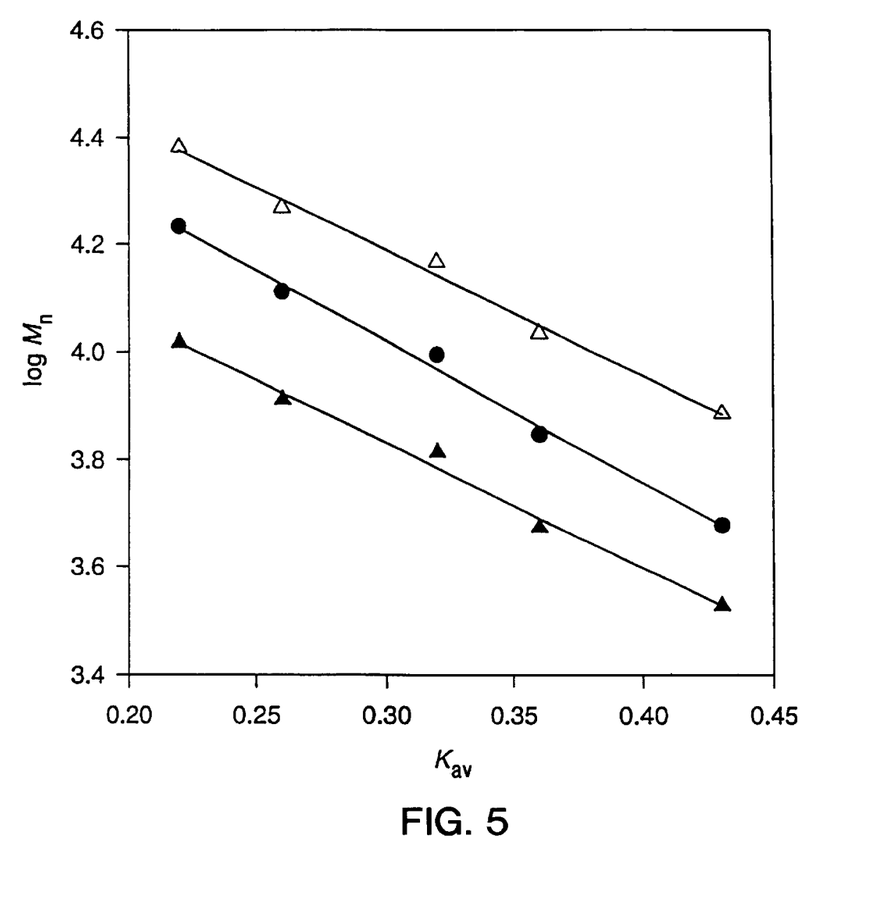
FIG. 5: Comparison of molar-mass determinations of [O]PRP fractions by SEC-MALLS/RI(·) and by colorimetry (see text) using glycolaldehyde (▲) or ribose (Δ) as standards in the $Cu^{2+}$/BCA procedure.

Both glycolaldehyde and ribose gave standard curves of high linearity ($r^2$:0.9985 for glycolaldehyde, 0.9980 for ribose) over a dynamic range of 2.5 to 25 nmol. Variability in the data did not exceed 5% RSD for triplicate ([O]-PRP) or guadruplicate (standards) analyses. The standard plots shown in FIG. 4 diverge significantly; their slopes indicate that the molar response of ribose was 2.3 times greater than that of glycolaldehyde. Molar masses (as $M_n$) for the [O]-PRP fragments (Table 5) estimated by these two curves were plotted against $K_{av}$ in FIG. 5, alongside the plot of the LLS data. The glycolaldehyde standard curve underestimates $L_n$ relative to the LLS data by 34–43%, whereas $L_n$ was overestimated by 33–50% using ribose as the standard. Although glycolaldehyde was a structurally rational choice as a standard, its ability to estimate the molar masses of the polysaccharide fragments was no better than that of ribose.

TABLE 5

Molar Masses of [O]-PRP Fractions by Colorimetric Reducing-End Group Analysis

| | Glycolaldehyde Standard | | Ribose Standard | |
|---|---|---|---|---|
| Sample | $L_n^a$ | $M_n$ (kg/mol) | $L_n^a$ | $M_n$ (kg/mol)$^b$ |
| I | 28 | 10.4 | 65 | 24.1 |
| II | 22 | 8.15 | 50 | 18.5 |
| III | 19 | 7.17 | 44 | 16.3 |
| IV | 13 | 4.72 | 29 | 10.8 |
| V | 9 | 3.37 | 21 | 7.69 |

$^a L_n$ = (nmol total Rib)/(nmol end groups ÷ 2); rounded to the nearest integer; nmol total Rib, from orcinol assay; nmol end groups, from BCA assay.
$^b M_n = 100 + [(L_n) (368 \text{ g mol}^{-1} \text{ NaPRP repeat units})]$; calculation gives $M_n$ in g/mol.

SEC-MALLS/RI and quantitative NMR determinations of the molar mass of [O]-PRP polysaccharides are superior to indirect methods because they are based on physical properties of the [O]-PRP molecules from which molar masses are calculated. The data from the two direct techniques corroborate each other; hence, quantitative NMR can be used to validate more practical molar-mass determinations based on SEC-MALLS/RI. Generation and analysis of narrow molar-mass standards derived from PRP of the present invention have been directly applied to routine molar-mass analysis of [O]-PRP samples by SEC-RI using a primary calibration curve.

Although the invention has been described in conjunction with a specific embodiment, it is evident that many alternatives and variations will be apparent to those skilled in the art in light of the foregoing description and annex drawings. Accordingly, the invention is intended to embrace all of the alternatives and variations that fall within the spirit and scope of the appended claims.

We claim:

1. A *Haemophilus influenzae* type b vaccine comprising *Haemophilus influenzae* type b capsular polysaccharide fragments, wherein the fragments are generated by oxidatively cleaving *Haemophilus influenzae* type b capsular polysaccharide, and wherein the fragments have the following repeat unit:

wherein n is between about 32 and about 59 as determined by the orcinol/Park-Johnson assay, and wherein the polysaccharide is conjugated to protein.

2. The vaccine according to claim 1, wherein n is between about 32 and about 42.

3. The vaccine according to claim 1, wherein said polysaccharide fragments have a molecular weight of between about 7,500 and about 15,000.

4. The vaccine according to claim 1, wherein said polysaccharide fragments have a molecular weight of between about 7,500 and about 10,000.

5. The vaccine according to claim 1, wherein n is between about 42 and about 59.

6. The vaccine according to claim 1, wherein said polysaccharide fragments have a molecular weight of between about 9500 and about 15,000.

* * * * *